United States Patent
Betancourt

(10) Patent No.: US 11,707,489 B2
(45) Date of Patent: Jul. 25, 2023

(54) ORAL DELIVERY OF THERAPEUTIC MAMMALIAN CELLS

(71) Applicant: Vitabolus, Inc., La Jolla, CA (US)

(72) Inventor: Aline M. Betancourt, La Jolla, CA (US)

(73) Assignee: RANAS, LLC, La Jolla, CA (US)

( * ) Notice: Subject to any disclaimer, the term of this patent is extended or adjusted under 35 U.S.C. 154(b) by 0 days.

(21) Appl. No.: 16/996,586

(22) Filed: Aug. 18, 2020

(65) Prior Publication Data

US 2020/0376039 A1    Dec. 3, 2020

Related U.S. Application Data

(63) Continuation of application No. PCT/US2019/058641, filed on Oct. 29, 2019.

(60) Provisional application No. 62/752,711, filed on Oct. 30, 2018.

(51) Int. Cl.
*A61K 9/48* (2006.01)
*A61K 35/28* (2015.01)
*A61P 1/00* (2006.01)

(52) U.S. Cl.
CPC ............ *A61K 35/28* (2013.01); *A61K 9/4808* (2013.01); *A61K 9/4841* (2013.01); *A61K 9/4866* (2013.01); *A61K 9/4891* (2013.01); *A61P 1/00* (2018.01)

(58) Field of Classification Search
None
See application file for complete search history.

(56) References Cited

U.S. PATENT DOCUMENTS

| | | |
|---|---|---|
| 2012/0027811 A1 | 2/2012 | Edwards et al. |
| 2012/0171230 A1 | 7/2012 | Lam et al. |
| 2014/0017787 A1 | 1/2014 | Betancourt |
| 2017/0258732 A1 | 9/2017 | Imran et al. |

FOREIGN PATENT DOCUMENTS

| | | |
|---|---|---|
| WO | WO-2016053758 A1 | 4/2016 |
| WO | WO-2017189621 A1 | 11/2017 |
| WO | WO-2018182612 A1 | 10/2018 |
| WO | WO-2018183941 A2 | 10/2018 |
| WO | WO-2020092421 A1 | 5/2020 |

OTHER PUBLICATIONS

Batorsky et al. Encapsulation of adult human mesenchymal stem cells within collagen-agarose microenvironments. Biotechnol Bioeng. 92(4):492-500 (2005).

Bartosh et al. Aggregation of human mesenchymal stromal cells (MSCs) into 3D spheroids enhances their antiinflammatory properties. PNAS USA 107:13724-13729 (2010).

Kremser et al. In vivo determination of the time and location of mucoadhesive drug delivery systems disintegration in the gastrointestinal tract. Magn Reson Imaging 26:638-643 (2008).

PCT/US2019/058641 International Search Report and Written Opinion dated Jan. 24, 2020.

(Continued)

*Primary Examiner* — Kevin S Orwig
(74) *Attorney, Agent, or Firm* — Wilson Sonsini Goodrich & Rosati

(57) ABSTRACT

Described herein are oral delivery systems for use in delivering live mammalian cells to the intestinal tract of an individual.

19 Claims, 10 Drawing Sheets

(56) References Cited

OTHER PUBLICATIONS

Pizzaro et al. Mouse models for the study of Crohn's disease. Trends Mol Med. 9(5):218-22 (2003).

Reix et al. Duodenum-specific drug delivery: in vivo assessment of a pharmaceutically developed enteric-coated capsule for a broad applicability in rat studies. Int J Pharm 422:338-340 (2012).

Saphier et al. Gastro intestinal tracking and gastric emptying of solid dosage forms in rats using X-ray imaging. Int J Pharm 388:190-195 (2010).

Sonaje et al. Enteric-coated capsules filled with freeze-dried chitosan/poly(gamma-glutamic acid) nanoparticles for oral insulin delivery. Biomaterials 31:3384-3394 (2010).

Tomaro-Duchesneau et al. Microencapsulation for the Therapeutic Delivery of Drugs, Live Mammalian and Bacterial Cells, and Other Biopharmaceutics: Current Status and Future Directions. J Pharm (Cairo) 2013:103527 (2013). Published online Dec. 4, 2012. doi: 10.1155/2013/103527.

U.S. Department of Health and Human Services Food and Drug Administration. Dissolution Testing of Immediate Release Solid Oral Dosage Forms. Guidance for Industry. Center for Drug Evaluation and Research (CDER). Aug. 1997. Section IV-A.

Waterman et al. A New mesenchymal stem cell (MSC) paradigm: Polarization into a pro-inflammatory MSC1 or an immunosuppressive MSC2 phenotype. PLOS ONE 5(4):e10088 (2010).

Su et al. Progress of clinical application of mesenchymal stem cells in the treatment of Crohn's disease. Chin J Diffie and Compl Cas 16(3):311-316 (2017) (English Abstract).

Zhao, Gang. Vitrification Preservation and 3D Culture of Stem Cells Based on Hydrogel Encapsulation. Wanfang Data Dissertation (Sep. 20, 2018) (English Abstract).

Shutz et al. Three-dimensional plotting of a cell-laden alginate/methylcellulose blend: towards biofabrication of tissue engineering constructs with clinically relevant dimensions. J Tissue Eng Regen Med 11 (5):1574-1587 (2017).

Single Capsule Monophasic Delivery

Capsule in Capsule Biphasic Delivery

| Table 1. Pharmacokinetics of Orally Delivered Live Cells | | |
|---|---|---|
| PARAMETERS | UNCOATED CONTROL Capsules | ENTERIC COATED CELL Capsules |
| Dose (Cell Number) | 5M | 5M |
| T max (hr) | 0 | 0.45+/-0.1 |
| Cell Viability (% live) | 0 | 87+/-6 |
| Cell Potency (cxcl9 cDNA expression) | FAIL | PASS |

FIG. 10

ORAL DELIVERY OF THERAPEUTIC MAMMALIAN CELLS

CROSS-REFERENCE

The present application is a continuation of International Application No. PCT/US2019/058641 filed Oct. 29, 2019, which claims the benefit of U.S. Provisional Patent Application No. 62/752,711, filed Oct. 30, 2018, entitled "ORAL DELIVERY OF THERAPEUTIC MAMMALIAN CELLS," the entire contents of which are incorporated herein by reference.

SUMMARY

The present disclosure relates to the development of a targeted delivery system for the oral delivery of live mammalian cells for various indications, including and not limited to aging-related or -associated diseases, acute and chronic inflammatory conditions, auto-immune disorders, neurological and neurodegenerative diseases, stroke, pain, and cancer. The present disclosure details methods to provide relief to immune and inflammatory disorders that are characteristic of these diseases among others, as well as, describes a cell therapy platform for site specific delivery of live therapeutic mammalian cells to the GI tract of a mammal, and/or the intestines and colon of a human subject.

In one aspect, described herein is, an oral delivery system; the system comprising: (a) a first capsule, the first capsule comprising a first plurality of live mammalian cells and a first enteric coating, wherein the first enteric coating releases the first plurality of live mammalian cells at a pH of about 6.2 to about 6.5; and (b) a second capsule, the second capsule comprising a second plurality of live mammalian cells, and a second enteric coating wherein the second enteric coating releases the second plurality of live mammalian cells at a pH of about 7 to 8; wherein the second capsule is surrounded by the first capsule. In certain embodiments, the first plurality of live mammalian cells and the second plurality of live mammalian cells are the same type of cell. In certain embodiments, the first plurality of live mammalian cells and the second plurality of live mammalian cells are different types of cells. In certain embodiments, the first plurality of live mammalian cells is targeted to the proximal colon and the second plurality of live mammalian cells is targeted to the ileum. In certain embodiments, the first plurality of live mammalian cells, and/or the second plurality of live mammalian cells comprise between about 10,000 and about 10 million live cells. In certain embodiments, the first plurality of live mammalian cells, and/or the second plurality of live mammalian cells comprise human cells. In certain embodiments, the first plurality of live mammalian cells, and/or the second plurality of live mammalian cells comprise multipotent cells. In certain embodiments, the multipotent cells comprise embryonic stem cells, pluripotent stem cells, induced pluripotent stem cells, mesenchymal stem cells, hematopoietic stem cells, myoblasts, fibroblasts, hepatic stem cells, kidney stem cells, heart stem cells, or intestinal stem cells. In certain embodiments, the first plurality of live mammalian cells, and/or the second plurality of live mammalian cells comprise immune cells. In certain embodiments, the immune cells comprise B cells, T cells, CD8+ T cells, CD4+ T cells, NK cells, dendritic cells, or macrophage cells. In certain embodiments, the first enteric coating comprises copolymers of methacrylic acid, copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein. In certain embodiments, the second enteric coating comprises copolymers of methacrylic acid, copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein. In certain embodiments, the first capsule, the second capsule, or the first capsule and the second capsule comprise a gel, an extracellular matrix protein, or an excipient. In certain embodiments, the gel comprises agar. In certain embodiments, the gel comprises a hydrogel. In certain embodiments, the extracellular matrix protein comprises collagen. In certain embodiments, the gel, matrix, or excipient preserves the viability of the first plurality of live mammalian cells, and/or the second plurality of live mammalian cells above about 80% viability for at least 14 days at 24° C. In certain embodiments, the oral delivery system is for use in delivery of live mammalian cells to the intestinal tract of an individual. In certain embodiments, the oral delivery system is for use in a method of treating a disease in an individual comprising orally administering the oral delivery system the individual. In certain embodiments, the oral delivery system is for use in a method of delivering live mammalian cells to the intestinal tract of an individual comprising orally administering the oral delivery system to the individual. In certain embodiments, the individual is a human.

In one aspect, described herein is, an oral delivery system; the system comprising: a capsule, the capsule comprising a plurality of live mammalian cells and an enteric coating, wherein the enteric coating releases the plurality of live mammalian cells at a pH of about 6.0 to about 8.0. In certain embodiments, the plurality of live mammalian cells are the same type of cell. In certain embodiments, the plurality of live mammalian cells are different types of cells. In certain embodiments, the enteric coating releases the plurality of live mammalian cells at a pH of about 6.2 to about 6.5. In certain embodiments, the enteric coating releases the plurality of live mammalian cells at a pH of about 7.0 to about 8.0. In certain embodiments, the plurality of live mammalian cells comprises between about 10,000 and about 10 million live cells. In certain embodiments, the plurality of live mammalian cells comprises human cells. In certain embodiments, the plurality of live mammalian cells comprises multipotent cells. In certain embodiments, the multipotent cells comprise embryonic stem cells, pluripotent stem cells, induced pluripotent stem cells, mesenchymal stem cells, hematopoietic stem cells, myoblasts, fibroblasts, hepatic stem cells, kidney stem cells, heart stem cells, or intestinal stem cells. In certain embodiments, the plurality of live mammalian cells, and/or the second plurality of live mammalian cells comprise immune cells. In certain embodiments, the immune cells comprise B cells, T cells, CD8+ T cells, CD4+ T cells, NK cells, dendritic cells, or macrophage cells. In certain embodiments, the enteric coating comprises copolymers of methacrylic acid, copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein. In certain embodiments, the first capsule, the second capsule, or the first capsule and the second capsule comprise a gel, an extracellular matrix protein, or an excipient. In certain embodiments, the gel comprises agar. In certain embodiments, the gel comprises a hydrogel. In certain embodiments, the extracellular matrix protein comprises collagen. In certain embodiments, the gel, matrix, or excipient preserves the viability of the plurality of live mammalian cells above about 80% viability for at least 14 days at 24° C. In certain embodiments, the oral delivery system is for use in delivery of live mammalian cells to the intestinal tract of an individual. In certain embodiments, the oral delivery system is for use in a method of treating a disease in an individual comprising orally administering the oral delivery system the individual. In certain embodiments, the oral delivery system is for use in a method of delivery of live mammalian cells to the intestinal tract of an individual comprising orally administering the oral delivery system the individual. In certain embodiments, the individual is a human.

In another aspect described herein is a composition of live mammalian cells formulated for oral delivery to an individual, the composition comprising (a) an enteric coating, (b) a matrix comprising about 1.0% to about 2.0% methyl cellulose and about 1.0% to about 2.0% alginate gel, and (c) a plurality of live mammalian cells, wherein the plurality of live mammalian cells is suspended in the matrix, and wherein the enteric coating surrounds the live mammalian cells suspended in the matrix. In certain embodiments, the matrix comprises about 1.3% to about 1.8% methylcellulose and about 1.3% to about 1.8% alginate gel. In certain embodiments, the matrix comprises about 1.5% methylcellulose and about 1.5% alginate gel. In certain embodiments, the methyl cellulose and alginate gel are present at a ratio of about 1:1. In certain embodiments, the enteric coating comprises methyl methacrylate-methacrylic acid copolymer (1:1). In certain embodiments, the enteric coating consists essentially of methyl methacrylate-methacrylic acid copolymer (1:1). In certain embodiments, the plurality of live mammalian cells comprises between about 10,000 and about 10 million live cells. In certain embodiments, the plurality of live mammalian cells comprises human cells. In certain embodiments, the plurality of live mammalian cells comprises non-human cells. In certain embodiments, the non-human animal cells are selected from canine cells, bovine cells, feline cells, porcine cells, equine cells, or ovine cells. In certain embodiments, the plurality of live mammalian cells comprises at least two types of cells. In certain embodiments, the plurality of live mammalian cells comprises multipotent cells. In certain embodiments, the multipotent cells comprise embryonic stem cells, pluripotent stem cells, induced pluripotent stem cells, mesenchymal stem cells, hematopoietic stem cells, myoblasts, fibroblasts, hepatic stem cells, kidney stem cells, heart stem cells, or intestinal stem cells. In certain embodiments, the multipotent cells comprise mesenchymal stem cells. In certain embodiments, the mesenchymal stem cells are Type 1 mesenchymal stem cells. In certain embodiments, the mesenchymal stem cells are Type 2 mesenchymal stem cells. In certain embodiments, the plurality of live mammalian cells, and/or the second plurality of live mammalian cells comprise immune cells. In certain embodiments, the immune cells comprise B cells, T cells, CD8+ T cells, CD4+ T cells, NK cells, dendritic cells, or macrophage cells. In certain embodiments, the composition preserves the viability of the first plurality of live mammalian cells, and/or the second plurality of live mammalian cells above about 80% viability for at least 14 days at 24° C. In certain embodiments, the matrix further comprises an extracellular matrix protein. In certain embodiments, the extracellular matrix protein comprises collagen. In certain embodiments, the live mammalian cell compositions are for use in treating an inflammatory or autoimmune disorder in a human. In certain embodiments, the inflammatory or autoimmune disorder is a gastrointestinal inflammatory or autoimmune disorder. In certain embodiments, the gastrointestinal inflammatory or autoimmune disorder comprises inflammatory bowel disease or Crohn's disease. In certain embodiments, the gastrointestinal inflammatory or autoimmune disorder comprises Crohn's disease. In certain embodiments, the live mammalian cell compositions are for use in treating an inflammatory or autoimmune disorder in an animal. In certain embodiments, the inflammatory or autoimmune disorder is a gastrointestinal inflammatory or autoimmune disorder. In certain embodiments, the live mammalian cell compositions are for use the animal is any one or more of a dog, a cow, a cat, a pig, a horse, or a sheep. Also described herein is a method of treating an inflammatory or autoimmune disorder in an individual comprising administering a dose of the composition of the cells to the alimentary canal of an individual. In certain embodiments, the live mammalian cell compositions are for use the individual is a human individual. In certain embodiments, the live mammalian cell compositions are for use the individual is a dog, a cow, a cat, a pig, a horse, or a sheep. In certain embodiments, the live mammalian cell compositions are for use the inflammatory or autoimmune disorder is a gastrointestinal inflammatory or autoimmune disorder. In certain embodiments, the live mammalian cell compositions are for use the gastrointestinal inflammatory or autoimmune disorder comprises inflammatory bowel disease or Crohn's disease. In certain embodiments, the live mammalian cell compositions are for use the gastrointestinal inflammatory or autoimmune disorder comprises Crohn's disease. Also described herein is a method of making a composition of live mammalian cells formulated for oral delivery comprising admixing a plurality of live mammalian cells with a matrix comprising about 1.0% to about 2.0% methyl cellulose and about 1.0% to about 2.0% alginate gel to provide a cell-matrix and applying an enteric coating to cell-matrix. In certain embodiments, the matrix comprises about 1.3% to about 1.8% methylcellulose and about 1.3% to about 1.8% alginate gel. In certain embodiments, the matrix comprises about 1.5% methylcellulose and about 1.5% alginate gel. In certain embodiments, methyl cellulose and alginate gel are present at a ratio of about 1:1. In certain embodiments, the enteric coating comprises methyl methacrylate-methacrylic acid copolymer (1:1). In certain embodiments, the plurality of live mammalian cells comprises between about 10,000 and about 10 million live cells. In certain embodiments, the plurality of live mammalian cells comprises human cells. In certain embodiments, the plurality of live mammalian cells comprises non-human cells.

BRIEF DESCRIPTION OF THE DRAWINGS

FIG. 10 shows a summary of pharmacokinetic parameters for live cells delivered by uncoated and coated capsules in mice following oral administration (n=3/ea). Maximum release profile of cells is expressed as hours elapsed for maximum recovery of cells. Cell viability was assessed by trypan blue exclusion assay. Cell potency was assessed by cDNA expression in recovered cells of the anti-inflammatory marker CXCL9.

DETAILED DESCRIPTION

Figure 1:
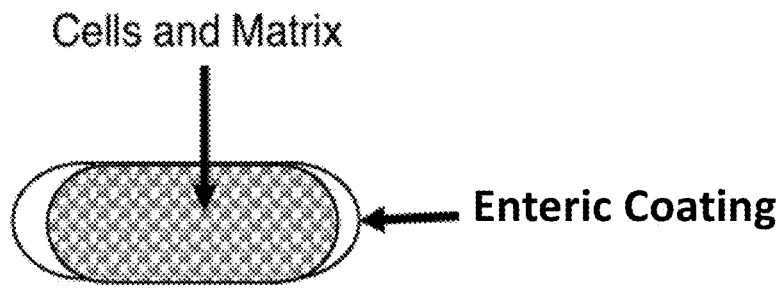
FIG. 1 illustrates a representative scheme of oral cell delivery capsules. The live therapeutic mammalian cells including but not limited to stem cells would be properly sourced and manufactured, loaded or admixed in a matrix, packaged into a capsule and finalized with enteric coating(s) in the single capsule monophasic delivery scheme on the top. In another embodiment, the live therapeutic mammalian cells including but not limited to stem cells would be properly sourced and manufactured, loaded or admixed in a matrix as before being packaged into one capsule. Subsequently, a second dose of live cells would be admixed in a matrix and packaged into a capsule that would next be loaded within the first capsule as shown in the capsule in capsule biphasic delivery scheme on the bottom.
Figure 1:
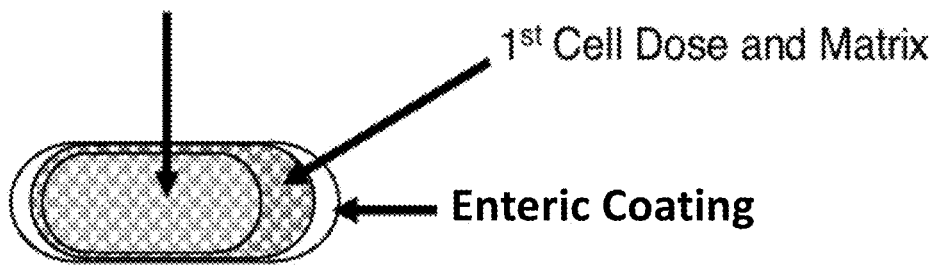

Described herein is an oral delivery system; the system comprising: (a) a first capsule, the first capsule comprising a first plurality of live mammalian cells and a first enteric coating, wherein the first enteric coating releases the first plurality of live mammalian cells at a pH of about 6.2 to about 6.5; and (b) a second capsule, the second capsule comprising a second plurality of live mammalian cells, and a second enteric coating wherein the second enteric coating releases the second plurality of live mammalian cells at a pH of about 7 to 8; wherein the second capsule is surrounded by the first capsule.

In another aspect described herein is an oral delivery system; the system comprising: a capsule, the capsule comprising a plurality of live mammalian cells and an enteric coating, wherein the enteric coating releases the plurality of live mammalian cells at a pH of about 6.0 to about 8.0.

In another aspect described herein is a composition of live mammalian cells formulated for oral delivery to an individual, the composition comprising (a) an enteric coating, (b) a matrix comprising from about 1.0% to about 2.0% methyl cellulose and about 1.0% to about 2.0% alginate gel, and (c) a plurality of live mammalian cells, wherein the plurality of live mammalian cells is suspended in the matrix, and wherein the enteric coating surrounds the live mammalian cells suspended in the matrix. In certain embodiments, the matrix comprises from about 1.3% to about 1.8% methylcellulose and from about 1.3% to about 1.8% alginate gel. In certain embodiments, the matrix comprises about 1.5% methylcellulose and about 1.5% alginate gel. In certain embodiments, the methyl cellulose and alginate gel are present at a ratio of about 1:1. In certain embodiments, the enteric coating comprises methyl methacrylate-methacrylic acid copolymer (1:1). In certain embodiments, the enteric coating consists essentially of methyl methacrylate-methacrylic acid copolymer (1:1). In certain embodiments, the plurality of live mammalian cells comprises between about 10,000 and about 10 million live cells. In certain embodiments, the plurality of live mammalian cells comprises human cells. In certain embodiments, the plurality of live mammalian cells comprises non-human cells.

In another aspect described herein is a composition of live mammalian cells formulated for oral delivery to an individual, the composition comprising (a) an enteric coating, (b) a matrix comprising from about 1.5% to about 1.5% methyl cellulose and about 1.5% to about 1.5% alginate gel, and (c) a plurality of live mammalian cells, wherein the plurality of live mammalian cells is suspended in the matrix, and wherein the enteric coating surrounds the live mammalian cells suspended in the matrix. In certain embodiments, the live mammalian cells are mesenchymal stem cells.

In another aspect described herein is a composition of live mammalian cells formulated for oral delivery to an individual, the composition comprising (a) an enteric coating, (b) a matrix comprising from about 1.4% to about 1.6% methyl cellulose and about 1.4% to about 1.6% alginate gel, and (c) a plurality of live mammalian cells, wherein the plurality of live mammalian cells is suspended in the matrix, and wherein the enteric coating surrounds the live mammalian cells suspended in the matrix. In certain embodiments, the live mammalian cells are mesenchymal stem cells.

Certain Definitions

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

"Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. Compositions for treating or preventing a given disease can consist essentially of the recited active ingredient, exclude additional active ingredients, but include other non-material components such as excipients, carriers, or diluents. "Consisting of" shall mean excluding more than trace elements of other ingredients and substantial method steps. Embodiments defined by each of these transition terms are within the scope of this disclosure.

As used herein the term "about" refers to an amount that is near the stated amount by 10%.

As used herein the term "individual," "patient," or "subject" refers to individuals diagnosed with, suspected of being afflicted with, or at-risk of developing at least one disease for which the described compositions and method are useful for treating. In certain embodiments, the individual is a mammal. In certain embodiments, the mammal is a mouse, rat, rabbit, dog, cat, horse, cow, sheep, pig, goat, llama, alpaca, or yak. In certain embodiments, the individual is a human.

As used herein the term "treat" or "treating" refers to interventions to a physiological or disease state of an individual designed or intended to ameliorate at least one sign or symptom associated with said physiological or disease state. The skilled artisan will recognize that given a heterogeneous population of individuals afflicted with a disease, not all individuals will respond equally, or at all, to a given treatment.

The term "multipotent stem cell" means a cell which is capable of giving rise to multiple different types of cells. The term "mesenchymal stem cell" means a stem cell originally derived from the mesenchyme. The term refers to a cell which is capable of differentiating into at least two or more of an osteoblast, a chondrocyte, an adipocyte, or a myocyte. Mesenchymal stem cells (MSC) are isolated from any type of adult tissue. Typically, mesenchymal stem cells are isolated from bone marrow, adipose tissue, umbilical cord, or peripheral blood. In a preferred aspect, MSCs are obtained from bone marrow or lipoaspirates, which are obtained from adipose tissue. The term "multipotent" or "pluripotent" also encompasses induced multipotent stem cells or induced pluripotent stem cells, or cells that have been induced to a pluripotent stage using any chemical or genetic means. In certain embodiments, the multipotent or pluripotent stem cells of the disclosure are mesenchymal stem cells.

The term "autoimmune disorder" refers to a condition in a subject characterized by cellular, tissue, and/or organ injury caused by an immunological reaction of the subject to its own cells, tissues, and/or organs.

The term "inflammatory disease" refers to a condition marked by increased activation of immune cells, secretion of cytokines, chemokines, or other factors that lead to immune cell activation or recruitment.

Oral Delivery Systems

Figure 2:
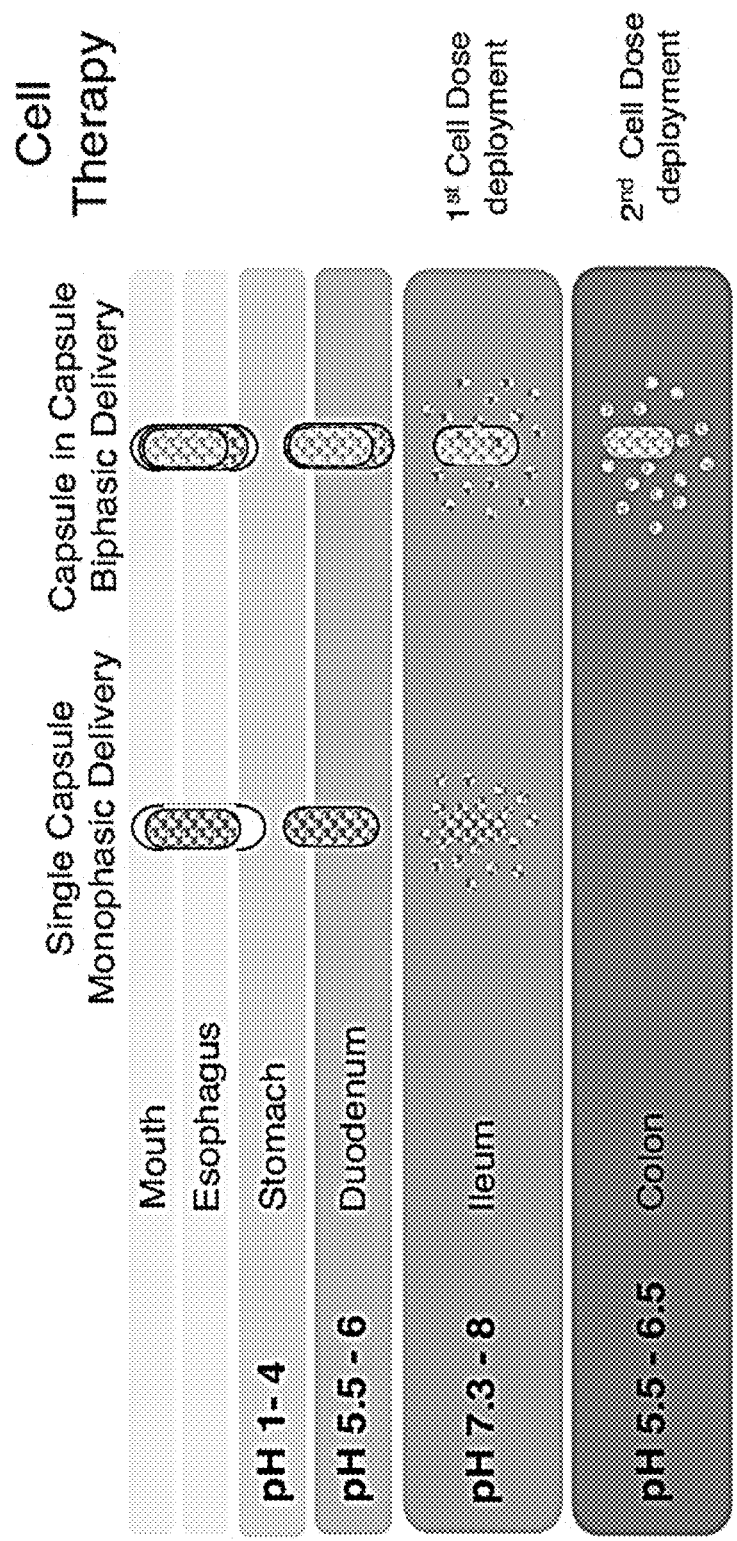
FIG. 2 illustrates a representative, non-limiting, scheme of oral delivery of the cell loaded capsules and their proposed deployment to the ileum and colon. The live therapeutic mammalian cells in the single capsule monophasic delivery (left) or the capsule in capsule biphasic delivery (right) would be taken orally and travel past the mouth, esophagus, and duodenum with the uncoating of the protective enteric coating and cell deployment occurring at the targeted ileum pH 7.3-8 and subsequent colon pH 5.5-6.5 as shown.
Figure 3:
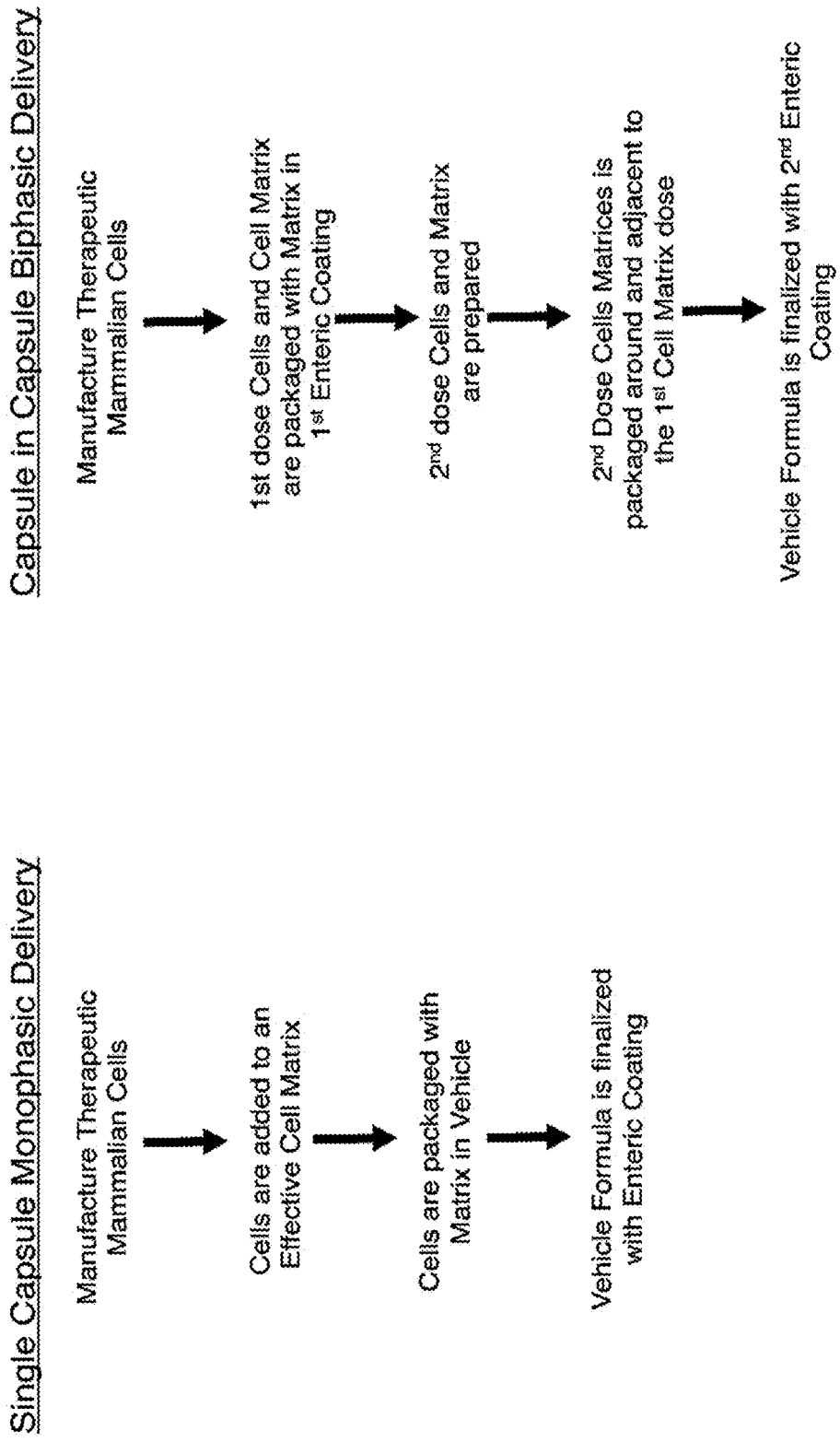
FIG. 3 illustrates a representative scheme of potential designs for oral cell delivery capsules. The live therapeutic mammalian cells including but not limited to stem cells would be properly sourced and manufactured, loaded or admixed in a matrix, packaged into a capsule and finalized with enteric coating(s) in the single capsule monophasic delivery scheme on the left. Alternatively, the live therapeutic mammalian cells including but not limited to stem cells would be properly sourced and manufactured, loaded or admixed in a matrix as before and packaged into one capsule. Subsequently, a second dose of live cells would be admixed in a matrix and packaged into a capsule that would next be loaded within the first capsule as shown in the capsule in capsule biphasic delivery scheme on right.

One aspect of the delivery systems described as shown in FIG. 1 is a monophasic delivery system. A monophasic delivery system comprises a plurality of cells and a pH sensitive enteric coating. Another aspect of the delivery systems described as shown in FIG. 1 is a biphasic delivery system. A biphasic delivery system comprises a first plurality of cells enclosed in an enteric coating, and a second plurality of cells in an enteric coating. The first plurality of cells surrounds the second plurality of cells, such that the first plurality of cells is released at a first pH, leaving the second plurality of cells to be released at a second pH. As a result, a biphasic delivery system can deliver two different pluralities of cells to two different locations in the alimentary canal of an individual as shown in FIG. 2. In certain embodiments, the first and the second plurality of cells comprise the same type of cell. In certain embodiments, the first and the second plurality of cells comprise different types of cells. In certain embodiments, the cells are embedded in a matrix and then surrounded by the enteric coating. The matrix serves to protect the cells from osmotic stress, pH stress, and mechanical disruption prior to release at the intended delivery site, which can comprise any one or more of the ileum, jejunum, duodenum, or colon. Systems such as these are useful in delivering therapeutic cells to an individual by an oral route. FIG. 3 provides an overview of a process for making and distributing the Oral live cell compositions described herein.

Uses

Described herein are systems useful for the oral delivery of live cells to the alimentary canal, lymph nodes, or circulation of a subject. The systems can be used to deliver cells across an intestinal barrier into the blood or lymphatic system by an oral route. The systems described herein can be used to deliver a therapeutic dose of mammalian cells to a subject. In certain embodiments, the systems are used to deliver a therapeutic dose of human cells to a human subject. In certain embodiments, the systems are used to deliver a therapeutic dose of human cells to a human subject diagnosed with, suspected of being afflicted with, or at risk of being afflicted with a disease or disorder.

In certain embodiments, the systems and live mammalian cell compositions deliver a therapeutic dose of cells to the colon (e.g. large intestine) of an individual diagnosed with, suspected of being afflicted with, or at risk of being afflicted with a disease or disorder. In certain embodiments, the systems deliver a therapeutic dose of cells to the small intestine of an individual diagnosed with, suspected of being afflicted with, or at risk of being afflicted with a disease or disorder. In certain embodiments, the systems deliver a therapeutic dose of cells to the ileum of an individual diagnosed with, suspected of being afflicted with, or at risk of being afflicted with a disease or disorder. In certain embodiments, the systems deliver a therapeutic dose of cells to the duodenum of an individual diagnosed with, suspected of being afflicted with, or at risk of being afflicted with a disease or disorder. In certain embodiments, the systems deliver a therapeutic dose of cells to the jejunum of an individual diagnosed with, suspected of being afflicted with, or at risk of being afflicted with a disease or disorder. In certain embodiments, the individual is a human individual and the cells are human cells.

The oral systems used herein are useful for delivering a therapeutic dose of live mammalian cells to domesticated animals for veterinary use. In certain embodiments, the systems deliver a therapeutic dose of canine cells to dogs. In certain embodiments, the systems deliver a therapeutic dose of canine cells to dogs with inflammatory bowel disease. In certain embodiments, the systems deliver a therapeutic dose of feline cells to cats. In certain embodiments, the systems deliver a therapeutic dose of bovine cells to bovine species. The oral systems described herein may also be mixed with food or nutritive feed to orally administer to animals. In certain embodiments, systems containing canine cells may be mixed with food to deliver to dogs. In certain embodiments, systems containing feline cells may be mixed with food to deliver to cats. In certain embodiments, systems containing bovine cells may be mixed with food or nutritive feed to deliver to bovine species.

The delivery systems and compositions of live mammalian cells are, in certain embodiments, for use in treating an inflammatory or autoimmune disorder in a human. In certain embodiments, the inflammatory or autoimmune disorder is a gastrointestinal inflammatory or autoimmune disorder. In certain embodiments, the gastrointestinal inflammatory or autoimmune disorder comprises inflammatory bowel disease or Crohn's disease. In certain embodiments, the gastrointestinal inflammatory or autoimmune disorder comprises Crohn's disease.

The delivery systems and compositions of live mammalian cells are, in certain embodiments, for use in treating an inflammatory or autoimmune disorder in an animal. In certain embodiments, the inflammatory or autoimmune disorder is a gastrointestinal inflammatory or autoimmune disorder. In certain embodiments, the animal is any one or more of a dog, a cow, a cat, a pig, a horse, or a sheep.

Cells

The oral delivery systems and compositions of live mammalian cells described herein are useful for delivery of live cells to the alimentary canal of a subject. In certain embodiments, the cells comprise eukaryotic cells. In certain embodiments, the cells comprise eukaryotic cells that lack a cell-wall. In certain embodiments, the cells comprise mammalian cells. In certain embodiments, the cells comprise human cells. In certain embodiments, the cells comprise the cells of a domestic animal selected from a cat, dog, pig, sheep, horse, cow, goat, yak, and any combination thereof. The cells to be included in the oral delivery systems are those that can deliver a therapeutic effect and halt, reduce, or ameliorate the symptoms of at least one disease associated with the subject, that the subject has been diagnosed with, or is suspected of being afflicted with. In certain embodiments, the disease is a disease of the digestive tract selected from Chron's disease or inflammatory bowel disease. In certain embodiments, the cells do not comprise prokaryotic cells.

Stem cells comprise one type of cell useful for inclusion in the oral delivery systems described herein. In certain embodiments, the oral delivery system comprises a plurality of stem cells. In certain embodiments, the stem cells comprise embryonic stem cells, pluripotent stem cells, adult stem cells, induced pluripotent stem cells, mesenchymal stem cells, hematopoietic stem cells, myoblasts, fibroblasts, hepatic stem cells, kidney stem cells, heart stem cells, or intestinal stem cells, or mixtures thereof. In certain embodiments, the cells comprise embryonic stem cells. In certain embodiments, the cells comprise mesenchymal stem cells. In certain embodiments, the cells comprise type I (pro-inflammatory) mesenchymal stem cells. In certain embodiments, the cells comprise type II (anti-inflammatory) mesenchymal stem cells. In certain embodiments, the cells comprise pluripotent or induced pluripotent stem cells. Type 1 or Type 2 mesenchymal stem cells can be made using TLR4 or TLR3 agonists respectively. Methods of making Type 1 or Type 2 mesenchymal stem cells are described in US2014/0017787 or WO2016053758A1 which are incorporated by reference herein in their entirety. In certain embodiments, the type 2 MSC express higher levels of CXCL9 than an MSC2 not induced with TLR3.

Immune cells are another type of cell useful for inclusion in the oral delivery systems described herein. In certain embodiments, the oral delivery system comprises a plurality of immune cells. In certain embodiments, the immune cells comprise B cells (e.g., CD19+ cells), T cells (e.g., CD3+ cells), CD8+ T cells, CD4+ T cells, NK cells, dendritic cells, or macrophage cells. In certain embodiments, the immune cells comprise T cells. In certain embodiments, the T cells comprise T cells with a regulatory T cell phenotype that express and secrete IL-10, express and secrete TGF-β, or that express the transcription factor FoxP3. In certain embodiments, the immune cells comprise NK cells. In certain embodiments, the immune cells comprise macrophages. In certain embodiments, the macrophages comprise M1 type (pro-inflammatory) macrophages. In certain embodiments, the macrophages comprise M2 type (suppressor) macrophages.

The oral delivery systems and compositions of live mammalian cells described herein, comprise in certain embodiments, mixtures of different cell types. In certain embodiments, the mixture comprises 2, 3, 4, 5, 6, 7, 8, 9, or more different cell types. In certain embodiments, the mixture comprises stem cells and immune cells. In certain embodiments, the mixture comprises different stem cell types. In certain embodiments, the mixture comprises different immune cell types. In certain embodiments, the mixture comprises stem cells and immune cells. The mixture can be in any ratio that is attractive for therapeutic treatment. In certain embodiments, two different cell types are included, and the ratio of a first type to a second type is 1:1, 1:2, 1:3, 1:4, 1:5, 1:6, 1:7, 1:8, or 1:9.

The oral delivery systems and compositions of live mammalian cells described herein comprises cells in a therapeutic amount. In certain embodiments, a therapeutic number of cells comprises between about $1 \times 10^4$ and about $1 \times 10^8$ cells, between about $1 \times 10^4$ and about $1 \times 10^7$ cells, between about $1 \times 10^5$ and about $1 \times 10^8$ cells, between about $1 \times 10^5$ and about $1 \times 10^7$ cells, or between about $1 \times 10^6$ and about $1 \times 10^8$ cells. In certain embodiments, a therapeutic number of cells comprises at least about $1 \times 10^4$, $2 \times 10^4$, $3 \times 10^4$, $4 \times 10^4$, $5 \times 10^4$, $6 \times 10^4$, $7 \times 104^5$, $8 \times 10^4$, or $9 \times 10^4$ cells. In certain embodiments, a therapeutic number of cells comprises at least about $1 \times 10^5$, $2 \times 10^5$, $3 \times 10^5$, $4 \times 10^5$, $5 \times 10^5$, $6 \times 10^5$, $7 \times 10^5$, $8 \times 10^5$, or $9 \times 10^5$ cells. In certain embodiments, a therapeutic number of cells comprises at least about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$ cells. In certain embodiments, a therapeutic number of cells comprises at least about $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$ cells. In certain embodiments, a therapeutic number of cells comprises no more than about $2 \times 10^4$, $3 \times 10^4$, $4 \times 10^4$, $5 \times 10^4$, $6 \times 10^4$, $7 \times 104^5$, $8 \times 10^4$, or $9 \times 10^4$ cells. In certain embodiments, a therapeutic number of cells comprises no more than about $1 \times 10^5$, $2 \times 10^5$, $3 \times 10^5$, $4 \times 10^5$, $5 \times 10^5$, $6 \times 10^5$, $7 \times 10^5$, $8 \times 10^5$, or $9 \times 10^5$ cells. In certain embodiments, a therapeutic number of cells comprises no more than about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$ cells. In certain embodiments, a therapeutic number of cells comprises no more than about $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$ cells. In certain embodiments, the cells are live cells, at least about 75%, 80%, 85%, 90%, 95%, 97%, 98%, 99% viable as determined by trypan blue staining.

For biphasic capsules that comprise distinct pluralities of cells each cell plurality comprises between about $1 \times 10^4$ and about $1 \times 10^8$ cells, between about $1 \times 10^4$ and about $1 \times 10^7$ cells, between about $1\times10^5$ and about $1\times10^8$ cells, between about $1\times10^5$ and about $1\times10^7$ cells, or between about $1\times10^6$ and about $1\times10^8$ cells. In certain embodiments, a therapeutic amount of cells comprises at least about $1\times10^4$, $2\times10^4$, $3\times10^4$, $4\times10^4$, $5\times10^4$, $6\times10^4$, $7\times10^{4 5}$, $8\times10^4$, or $9\times10^4$ cells. In certain embodiments, each cell plurality comprises at least about $1\times10^5$, $2\times10^5$, $3\times10^5$, $4\times10^5$, $5\times10^5$, $6\times10^5$, $7\times10^5$, $8\times10^5$, or $9\times10^5$ cells. In certain embodiments, each cell plurality comprises at least about $1\times10^6$, $2\times10^6$, $3\times10^6$, $4\times10^6$, $5\times10^6$, $6\times10^6$, $7\times10^6$, $8\times10^6$, $9\times10^6$ cells. In certain embodiments, each cell plurality comprises at least about $1\times10^7$, $2\times10^7$, $3\times10^7$, $4\times10^7$, $5\times10^7$, $6\times10^7$, $7\times10^7$, $8\times10^7$, $9\times10^7$ cells. In certain embodiments, each cell plurality comprises no more than about $2\times10^4$, $3\times10^4$, $4\times10^4$, $5\times10^4$, $6\times10^4$, $7\times10^{4 5}$, $8\times10^4$, or $9\times10^4$ cells. In certain embodiments, each cell plurality comprises no more than about $1\times10^5$, $2\times10^5$, $3\times10^5$, $4\times10^5$, $5\times10^5$, $6\times10^5$, $7\times10^5$, $8\times10^5$, or $9\times10^5$ cells. In certain embodiments, each cell plurality comprises no more than about $1\times10^6$, $2\times10^6$, $3\times10^6$, $4\times10^6$, $5\times10^6$, $6\times10^6$, $7\times10^6$, $8\times10^6$, $9\times10^6$ cells. In certain embodiments, each cell plurality comprises no more than about $1\times10^7$, $2\times10^7$, $3\times10^7$, $4\times10^7$, $5\times10^7$, $6\times10^7$, $7\times10^7$, $8\times10^7$, $9\times10^7$, $1\times10^8$ cells. In certain embodiments, the cells in a biphasic formulation are live cells, at least about 75%, 80%, 85%, 90%, 95%, 97%, 98%, 99% viable as determined by trypan blue staining.

Matrix

The cells of the currently described oral delivery systems and compositions of live mammalian cells comprise, or are embedded in a matrix, gel or, excipient. The matrix serves to protect live cells from dehydration, osmotic stress, pH stress, protease degradation, and other stresses present in the GI system. In certain embodiments, the cells are embedded or suspended in a matrix. In certain embodiments, the matrix comprises agar. In certain embodiments, the matrix comprises methyl cellulose. In certain embodiments, the matrix comprises alginate. In certain embodiments, the matrix comprises methyl cellulose and alginate. In certain embodiments, the matrix comprises methyl cellulose and alginate in approximately equal amounts. In certain embodiments, the matrix comprises a hydrogel. Suitable hydrogels include those derived from collagen, hyaluronate, hyaluronan, fibrin, alginate, agarose, chitosan, and combinations thereof. In other embodiments, suitable hydrogels are synthetic polymers. In further embodiments, suitable matrices for embedding live cells include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, Novo-Gel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), or combinations thereof.

In certain embodiments the matrix comprises alginate gel and methyl cellulose in approximately equal amounts.

In certain embodiments, the matrix comprises live cells mixed with alginate gel and methyl cellulose at a given ratio. In certain embodiments, the ratio of alginate gel to methyl cellulose in the matrix is about 1:0.1, about 1:0.2, about 1:0.3 about 1:0.4, about 1:0.5, about 1:0.6, about 1:0.7, about 1:0.8, about 1:0.9, about 1:1, about 1:1.1, about 1:1.2, about 1:1.3, about 1:1.4, about 1:1.5, about 1:1.6, about 1:1.7, about 1:1.8, about 1:1.9, or about 1:2. In certain embodiments, the ratio of methyl cellulose to alginate gel in the matrix is about 1:0.1, about 1:0.2, about 1:0.3 about 1:0.4, about 1:0.5, about 1:0.6, about 1:0.7, about 1:0.8, about 1:0.9, about 1:1, about 1:1.1, about 1:1.2, about 1:1.3, about 1:1.4, about 1:1.5, about 1:1.6, about 1:1.7, about 1:1.8, about 1:1.9, or about 1:2.

Alternatively, in certain embodiments, this mixture of alginate gel and methyl cellulose may contain different concentrations of methyl cellulose. In certain embodiments, the concentration of alginate gel is about 0.5% to about 3.0%. In certain embodiments, the concentration of alginate gel is at least about 0.5%. In certain embodiments, the concentration of alginate gel is at most about 3.0%. In certain embodiments, the concentration of alginate gel is about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%. In certain embodiments, the concentration of alginate gel is at least about 0.5%, at least about 0.6%, at least about 0.7%, at least about 0.8%, at least about 0.9%, at least about 1.0%, at least about 1.1%, at least about 1.2%, at least about 1.3%, or at least about 1.4%. In certain embodiments, the concentration of alginate gel is at most about 3.0% at most about 2.9%, at most about 2.8%, at most about 2.7%, at most about 2.6%, at most about 2.5%, at most about 2.4%, at most about 2.3%, at most about 2.2%, at most about 2.1%, at most about 2.0%, at most about 1.9%, at most about 1.8%, at most about 1.7%, at most about 1.6%, or at most about 1.5%. In certain embodiments, the concentration of alginate gel is about 0.5% to about 0.7%, about 0.5% to about 0.9%, about 0.5% to about 1.1%, about 0.5% to about 1.3%, about 0.5% to about 1.5%, about 0.5% to about 1.7%, about 0.5% to about 1.9%, about 0.5% to about 2.1%, about 0.5% to about 2.5%, about 0.5% to about 2.7%, about 0.5% to about 2.9%, about 0.7% to about 0.9%, about 0.7% to about 1.1%, about 0.7% to about 1.3%, about 0.7% to about 1.5%, about 0.7% to about 1.7%, about 0.7% to about 1.9%, about 0.7% to about 2.1%, about 0.7% to about 2.5%, about 0.7% to about 2.7%, about 0.7% to about 2.9%, about 0.9% to about 1.1%, about 0.9% to about 1.3%, about 0.9% to about 1.5%, about 0.9% to about 1.7%, about 0.9% to about 1.9%, about 0.9% to about 2.1%, about 0.9% to about 2.5%, about 0.9% to about 2.7%, about 0.9% to about 2.9%, about 1.1% to about 1.3%, about 1.1% to about 1.5%, about 1.1% to about 1.7%, about 1.1% to about 1.9%, about 1.1% to about 2.1%, about 1.1% to about 2.5%, about 1.1% to about 2.7%, about 1.1% to about 2.9%, about 1.3% to about 1.5%, about 1.3% to about 1.7%, about 1.3% to about 1.9%, about 1.3% to about 2.1%, about 1.3% to about 2.5%, about 1.3% to about 2.7%, about 1.3% to about 2.9%, about 1.5% to about 1.7%, about 1.5% to about 1.9%, about 1.5% to about 2.1%, about 1.5% to about 2.5%, about 1.5% to about 2.7%, about 1.5% to about 2.9%, about 1.7% to about 1.9%, about 1.7% to about 2.1%, about 1.7% to about 2.5%, about 1.7% to about 2.7%, about 1.7% to about 2.9%, about 1.9% to about 2.1%, about 1.9% to about 2.5%, about 1.9% to about 2.7%, about 1.9% to about 2.9%, about 2.1% to about 2.5%, about 2.1% to about 2.7%, about 2.1% to about 2.9%, about 2.5% to about 2.7%, about 2.5% to about 2.9%, or about 2.7% to about 2.9%. In certain embodiments, the concentration of methyl cellulose is about 0.5% to about 3.0%. In certain embodiments, the concentration of methyl cellulose is at least about 0.5%. In certain embodiments, the concentration of methyl cellulose is at most about 3.0%. In certain embodiments, the concentration of methyl cellulose is about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%. In certain embodiments, the concentration of methyl cellulose is at least about 0.5%, at least about 0.6%, at least about 0.7%, at least about 0.8%, at least about 0.9%, at least about 1.0%, at least about 1.1%, at least about 1.2%, at least about 1.3%, or at least about 1.4%. In certain embodiments, the concentration of methyl cellulose is at most about 3.0% at most about 2.9%, at most about 2.8%, at most about 2.7%, at most about 2.6%, at most about 2.5%, at most about 2.4%, at most about 2.3%, at most about 2.2%, at most about 2.1%, at most about 2.0%, at most about 1.9%, at most about 1.8%, at most about 1.7%, at most about 1.6%, or at most about 1.5%. In certain embodiments, the concentration of methyl cellulose is about 0.5% to about 0.7%, about 0.5% to about 0.9%, about 0.5% to about 1.1%, about 0.5% to about 1.3%, about 0.5% to about 1.5%, about 0.5% to about 1.7%, about 0.5% to about 1.9%, about 0.5% to about 2.1%, about 0.5% to about 2.5%, about 0.5% to about 2.7%, about 0.5% to about 2.9%, about 0.7% to about 0.9%, about 0.7% to about 1.1%, about 0.7% to about 1.3%, about 0.7% to about 1.5%, about 0.7% to about 1.7%, about 0.7% to about 1.9%, about 0.7% to about 2.1%, about 0.7% to about 2.5%, about 0.7% to about 2.7%, about 0.7% to about 2.9%, about 0.9% to about 1.1%, about 0.9% to about 1.3%, about 0.9% to about 1.5%, about 0.9% to about 1.7%, about 0.9% to about 1.9%, about 0.9% to about 2.1%, about 0.9% to about 2.5%, about 0.9% to about 2.7%, about 0.9% to about 2.9%, about 1.1% to about 1.3%, about 1.1% to about 1.5%, about 1.1% to about 1.7%, about 1.1% to about 1.9%, about 1.1% to about 2.1%, about 1.1% to about 2.5%, about 1.1% to about 2.7%, about 1.1% to about 2.9%, about 1.3% to about 1.5%, about 1.3% to about 1.7%, about 1.3% to about 1.9%, about 1.3% to about 2.1%, about 1.3% to about 2.5%, about 1.3% to about 2.7%, about 1.3% to about 2.9%, about 1.5% to about 1.7%, about 1.5% to about 1.9%, about 1.5% to about 2.1%, about 1.5% to about 2.5%, about 1.5% to about 2.7%, about 1.5% to about 2.9%, about 1.7% to about 1.9%, about 1.7% to about 2.1%, about 1.7% to about 2.5%, about 1.7% to about 2.7%, about 1.7% to about 2.9%, about 1.9% to about 2.1%, about 1.9% to about 2.5%, about 1.9% to about 2.7%, about 1.9% to about 2.9%, about 2.1% to about 2.5%, about 2.1% to about 2.7%, about 2.1% to about 2.9%, about 2.5% to about 2.7%, about 2.5% to about 2.9%, or about 2.7% to about 2.9%.

In some embodiments, the matrix comprises live mammalian cells mixed with a matrix of about 0.5% to about 3.0% alginate gel and about 0.5% to about 3.0% methyl cellulose. The cell gel mixture is then transferred to an enteric-coated capsule. In certain embodiments, the capsule is coated with methyl methacrylate-methacrylic acid copolymer (1:1). In certain embodiments, the live mammalian cells comprise mesenchymal stem cells.

In some embodiments, the matrix comprises live mammalian cells mixed with a matrix of about 1.5% alginate gel and about 1.5% methyl cellulose. The cell gel mixture is then transferred to an enteric-coated capsule. In certain embodiments, the capsule is coated with methyl methacrylate-methacrylic acid copolymer (1:1). In certain embodiments, the live mammalian cells comprise mesenchymal stem cells.

In some embodiments, the matrix comprises live mammalian cells suspended in mixture of about 0.5% to about 3.0% alginate gel and about 0.5% to about 3.0% methyl cellulose, in a capsule coated with methyl methacrylate-methacrylic acid copolymer (1:1). In certain embodiments, the live mammalian cells comprise mesenchymal stem cells.

In some embodiments, the matrix comprises live mammalian cells suspended in mixture of about 1.0% to about 2.5% alginate gel and about 1.0% to about 2.5% methyl cellulose, in a capsule coated with methyl methacrylate-methacrylic acid copolymer (1:1). In certain embodiments, the live mammalian cells comprise mesenchymal stem cells.

In some embodiments, the matrix comprises live mammalian cells suspended in mixture of about 1.0% to about 2.0% alginate gel and about 1.0% to about 2.0% methyl cellulose, in a capsule coated with methyl methacrylate-methacrylic acid copolymer (1:1). In certain embodiments, the live mammalian cells comprise mesenchymal stem cells.

In some embodiments, the matrix comprises live mammalian cells suspended in mixture of about 1.2% to about 1.8% alginate gel and about 1.2% to about 1.8% methyl cellulose, in a capsule coated with methyl methacrylate-methacrylic acid copolymer (1:1).

In some embodiments, the matrix comprises live mammalian cells suspended in mixture of about 1.4% to about 1.6% alginate gel and about 1.4% to about 1.6% methyl cellulose, in a capsule coated with methyl methacrylate-methacrylic acid copolymer (1:1). In certain embodiments, the live mammalian cells comprise mesenchymal stem cells.

In some embodiments, the matrix comprises live mammalian cells suspended in mixture of about 1.5% alginate gel and about 1.5% methyl cellulose, in a capsule coated with methyl methacrylate-methacrylic acid copolymer (1:1). In certain embodiments, the live mammalian cells comprise mesenchymal stem cells.

In certain embodiments, the matrix comprises live cells and agar at a given concentration. In certain embodiments, the concentration of agar in the matrix is between about 0.1% w/v and about 10% w/v, between about 0.1% w/v and about 8% w/v, between about 0.1% w/v and about 5% w/v, between about 0.1% w/v and about 4% w/v, between about 0.1% w/v and about 3% w/v, between about 0.1% w/v and about 2% w/v, between about 0.1% w/v and about 1% w/v, between about 0.2% w/v and about 10% w/v, between about 0.2% w/v and about 8% w/v, between about 0.2% w/v and about 5% w/v, between about 0.2% w/v and about 4% w/v, between about 0.2% w/v and about 3% w/v, between about 0.2% w/v and about 2% w/v, between about 0.2% w/v and about 1% w/v, between about 0.4% w/v and about 10% w/v, between about 0.4% w/v and about 8% w/v, between about 0.4% w/v and about 5% w/v, between about 0.4% w/v and about 4% w/v, between about 0.4% w/v and about 3% w/v, between about 0.4% w/v and about 2% w/v, between about 0.4% w/v and about 1% w/v, between about 0.5% w/v and about 10% w/v, between about 0.5% w/v and about 8% w/v, between about 0.5% w/v and about 5% w/v, between about 0.5% w/v and about 4% w/v, between about 0.5% w/v and about 3% w/v, between about 0.5% w/v and about 2% w/v, between about 0.5% w/v and about 1% w/v. In certain embodiments, the concentration of Agar in the matrix is about 0.1%, 0.2%, 0.3%, 0.4%, 0.5%, 0.6%, 0.7%, 0.8%, 0.9%, or 1.0%. In certain embodiments, the concentration of Agar in the matrix is about 1.0%, 2.0%, 3.0%, 4.0%, 5.0%, 6.0%, 7.0%, 8.0%, 9.0%, or 10%.

The matrixes described herein have a given viscosity. In further embodiments, the matrix comprising the cells is characterized by having a viscosity of between about 500 and 1,000,000 centipoise; between about 1000 and 1,000,000 centipoise; between about 1,000 and 500,000 centipoise; between about 10,000 and 500,000 centipoise; between about 10,000 and 400,000 centipoise; between about 10,000 and 3000,000 centipoise; between about 100,000 and 1,000,000 centipoise; or between about 500,000 and 1,000,000 centipoise.

In certain embodiments, the matrix comprises additional molecules such as an extracellular matrix protein, like collagen or fibrin; a carbohydrate, such as glucose, dextrose, or sucrose; fibers, such as cellulose; a vitamin or mineral; buffers, isotonic solutions, or amino acids.

Coatings

The oral delivery systems herein comprise a coating formulated to dissolve at a certain pH. For biphasic delivery the oral delivery systems comprise two coatings formulated to dissolve at different pHs. In certain embodiments, the coatings are formulated to dissolve at a pH of about 5.5 to about 6.0 in order to target the duodenum; at a pH of about 7.3 to about 8.0 to target the ileum; or a pH of about 5.5 to about 6.5 to target the colon. In certain embodiments, the coating is formulated to dissolve at a pH of about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. In certain embodiments, for biphasic delivery one coating is formulated at a pH of about 7.3 to about 8.0 to target the ileum; and one coating at a pH of about 5.5 to about 6.5 to target the colon. In certain embodiments, for biphasic delivery one coating is formulated at a pH of about 5.5 to about 6.0 to target the duodenum; and one coating at a pH of about 5.5 to about 6.5 to target the colon. In certain embodiments, for biphasic delivery one coating is formulated at a pH of about 5.5 to about 6.0 to target the duodenum; and one coating at a pH of about 7.3 to about 8.0 to target the ileum.

Also contemplated are enteric cell formulations including a disclosed cell or population of cells and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials that can be included in the oral delivery systems and compositions of live mammalian cells described herein include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

Biphasic capsules comprising live mammalian cells comprise a first and a second enteric coating. In certain embodiments, the first enteric coating comprises copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein. In certain embodiments, the second enteric coating comprises copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein. In certain embodiments, the first enteric coating comprises copolymers of methacrylic acid. In certain embodiments, the second enteric coating comprises copolymers of methacrylic acid.

In certain embodiments, an enteric coating of the live mammalian cell compositions described herein comprise methyl methacrylate-methacrylic acid copolymer (1:1).

In certain embodiments, the gel, matrix, or excipient along with an enteric coating preserves the viability of the first plurality of live mammalian cells, and/or the second plurality of live mammalian cells at about 80-85% viability. In certain embodiments the gel, matrix or excipient preserves the viability of the first plurality of live mammalian cells, and/or the second plurality of live mammalian cells above about 50%, 60%, 70%, or 80% viability for at least 2, 3, 4, 5, 6, 7, 8, 9, 10 days at 24° C.

In certain embodiments, the gel, matrix along with an enteric coating or excipient provides a $T_{max}$ of about 0.4 to 0.6 hours. In certain embodiments, the gel, matrix or excipient provides a $T_{max}$ of about 0.4 hours, about 0.41 hours, about 0.42 hours, about 0.43 hours, about 0.44 hours, about 0.45 hours, about 0.46 hours, about 0.47 hours, about 0.48 hours, about 0.49 hours, about 0.50 hours, about 0.51 hours, about 0.52 hours, about 0.53 hours, about 0.54 hours, about 0.55 hours, about 0.56 hours, about 0.57 hours, about 0.58 hours, about 0.59 hours, or about 0.60 hours. In certain embodiments, the gel, matrix or excipient provides a $T_{max}$ of at least about 0.4 hours, at least about 0.4 hours, at least about 0.42 hours, at least about 0.43 hours, at least about 0.44 hours, or at least about 0.45 hours. In certain embodiments, the gel, matrix or excipient provides a $T_{max}$ of at most about 0.46 hours, at most about 0.47 hours, at most about 0.48 hours, at most about 0.49 hours, at most about 0.50 hours, at most about 0.51 hours, at most about 0.52 hours, at most about 0.53 hours, at most about 0.54 hours, at most about 0.55 hours, at most about 0.56 hours, at most about 0.57 hours, at most about 0.58 hours, at most about 0.59 hours, or at most about 0.60 hours.

Methods of Making Oral Delivery Systems

In certain embodiments, also described herein are methods of making oral delivery systems comprising admixing a live cell population with a matrix described herein and contacting the matrix:live cell population composition with an enteric coating. In certain embodiments, the matrix:live cell composition is added to a capsule before an enteric coating. In certain embodiments, also described herein are methods of making oral delivery systems comprising admixing a live cell population with a matrix comprising agar described herein and contacting the matrix:live cell population composition with an enteric coating comprising a copolymer of methacrylic acid.

In another aspect a method of making a composition of live mammalian cells formulated for oral delivery comprises admixing a plurality of live mammalian cells with a matrix comprising from about 1.0% to about 2.0% methyl cellulose and about 1.0% to about 2.0% alginate gel to provide a cell-matrix, and applying an enteric coating to cell-matrix. In certain embodiments, the matrix comprises from about 1.3% to about 1.8% methylcellulose and from about 1.3% to about 1.8% alginate gel. In certain embodiments, the matrix comprises about 1.5% methylcellulose and about 1.5% alginate gel. In certain embodiments, the methyl cellulose and alginate gel are present at a ratio of about 1:1. In certain embodiments, the enteric coating comprises methyl methacrylate-methacrylic acid copolymer (1:1). In certain embodiments, the plurality of live mammalian cells comprises between about 10,000 and about 10 million live cells. In certain embodiments, the plurality of live mammalian cells comprises human cells. In certain embodiments, the plurality of live mammalian cells comprises non-human cells.

Further Embodiments

The further specific numbered embodiments are contemplated herein:
1. An oral delivery system; the system comprising:
   a) a first capsule, the first capsule comprising a first plurality of live mammalian cells and a first enteric coating, wherein the first enteric coating releases the first plurality of live mammalian cells at a pH of about 6.2 to about 6.5; and
   b) a second capsule, the second capsule comprising a second plurality of live mammalian cells, and a second enteric coating wherein the second enteric coating releases the second plurality of live mammalian cells at a pH of about 7 to about 8;
   wherein the second capsule is surrounded by the first capsule.
2. The oral delivery system of embodiments 1, wherein the first plurality of live mammalian cells and the second plurality of live mammalian cells are the same type of cell.
3. The oral delivery system of embodiment 1, wherein the first plurality of live mammalian cells and the second plurality of live mammalian cells are different types of cells.
4. The oral delivery system of any one of embodiments 1 to 3, wherein the first plurality of live mammalian cells is targeted to the proximal colon and the second plurality of live mammalian cells is targeted to the ileum.
5. The oral delivery system of any one of embodiments 1 to 4, wherein the first plurality of live mammalian cells, and/or the second plurality of live mammalian cells comprise between about 10,000 and about 10 million live cells.
6. The oral delivery system of any one of embodiments 1 to 5, wherein the first plurality of live mammalian cells, and/or the second plurality of live mammalian cells comprise human cells.
7. The oral delivery system of any one of embodiments 1 to 6, wherein the first plurality of live mammalian cells, and/or the second plurality of live mammalian cells comprise multipotent cells.
8. The oral delivery system of embodiment 7, wherein the multipotent cells comprise embryonic stem cells, pluripotent stem cells, induced pluripotent stem cells, mesenchymal stem cells, hematopoietic stem cells, myoblasts, fibroblasts, hepatic stem cells, kidney stem cells, heart stem cells, or intestinal stem cells.
9. The oral delivery system of any one of embodiments 1 to 6, wherein the first plurality of live mammalian cells, and/or the second plurality of live mammalian cells comprise immune cells.
10. The oral delivery system of embodiment 9, wherein the immune cells comprises B cells, T cells, CD8+ T cells, CD4+ T cells, NK cells, dendritic cells, or macrophage cells.
11. The oral delivery system of any one of embodiments 1 to 10, wherein the first enteric coating comprises copolymers of methacrylic acid, copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein.
12. The oral delivery system of any one of embodiments 1 to 11, wherein the second enteric coating comprises copolymers of methacrylic acid, copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein.
13. The oral delivery system of any one of embodiments 1 to 12, wherein the first capsule, the second capsule, or the first capsule and the second capsule comprise a gel, a matrix, an extracellular matrix protein, or an excipient.
14. The oral delivery system of embodiment 13, wherein the gel comprises agar.
15. The oral delivery system of embodiment 13, wherein the gel comprises a hydrogel.
16. The oral delivery system of embodiment 13, wherein the extracellular matrix protein comprises collagen.
17. The oral delivery system of any one of embodiments 1 to 16, wherein the gel, matrix, or excipient preserves the viability of the first plurality of live mammalian cells, and/or the second plurality of live mammalian cells above about 80% viability for at least 14 days at 24° C.
18. The oral delivery system of any one of embodiments 1 to 17, for use in delivery of live mammalian cells to the intestinal tract of an individual.
19. The oral delivery system of any one of embodiments 1 to 17, for use in delivery of live mammalian cells to intestinal tract of a domesticated animal for veterinary use.
20. A method of delivering live mammalian cells to the intestinal tract of an individual comprising orally administering the oral delivery system of any one of embodiments 1 to 17 to the individual.
21. The method of embodiment 20, wherein the individual is a human.
22. The method of embodiment 20, wherein said individual is a domesticated animal.
23. An oral delivery system; the system comprising:
   a) a capsule, the capsule comprising a plurality of live mammalian cells and an enteric coating, wherein the enteric coating releases the plurality of live mammalian cells at a pH of about 6.0 to about 8.0.
24. The oral delivery system of embodiment 23, wherein the plurality of live mammalian cells are the same type of cell.

25. The oral delivery system of embodiment 23, wherein the plurality of live mammalian cells are different types of cells.

26. The oral delivery system of embodiment 23, wherein the enteric coating releases the plurality of live mammalian cells at a pH of about 6.2 to about 6.5.

27. The oral delivery system of embodiment 23, wherein the enteric coating releases the plurality of live mammalian cells at a pH of about 7.0 to about 8.0.

28. The oral delivery system of any one of embodiments 23 to 27, wherein the plurality of live mammalian cells comprises between about 10,000 and about 10 million live cells.

29. The oral delivery system of any one of embodiments 23 to 28, wherein the plurality of live mammalian cells comprises human cells.

30. The oral delivery system of any one of embodiments 23 to 29, wherein the plurality of live mammalian cells comprises multipotent cells.

31. The oral delivery system of any one of embodiments 23 to 30, wherein the multipotent cells comprise embryonic stem cells, pluripotent stem cells, induced pluripotent stem cells, mesenchymal stem cells, hematopoietic stem cells, myoblasts, fibroblasts, hepatic stem cells, kidney stem cells, heart stem cells, or intestinal stem cells.

32. The oral delivery system of any one of embodiments 23 to 31, wherein the plurality of live mammalian cells, and/or the second plurality of live mammalian cells comprise immune cells.

33. The oral delivery system of embodiment 32, wherein the immune cells comprises B cells, T cells, CD8+ T cells, CD4+ T cells, NK cells, dendritic cells, or macrophage cells.

34. The oral delivery system of any one of embodiments 23 to 33, wherein the enteric coating comprises copolymers of methacrylic acid, copolymers of methacrylic acid, methyl methacrylate, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, or zein.

35. The oral delivery system of any one of embodiments 23 to 34, wherein the first capsule, the second capsule, or the first capsule and the second capsule comprise a gel, an extracellular matrix protein, or an excipient.

36. The oral delivery system of embodiment 35, wherein the gel comprises agar.

37. The oral delivery system of embodiment 35, wherein the gel comprises a hydrogel.

38. The oral delivery system of embodiment 35, wherein the extracellular matrix protein comprises collagen.

39. The oral delivery system of any one of embodiments 23 to 38, wherein the gel, matrix, or excipient preserves the viability of the plurality of live mammalian cells above about 80% viability for at least 14 days at 24° C.

40. The oral delivery system of any one of embodiments 23 to 39, for use in delivery of live mammalian cells to the intestinal tract of an individual.

41. A method of treating a disease in an individual comprising orally administering the oral delivery system of any one of embodiments 23 to 40 to the individual.

42. A method of treating a disease in a domesticated animal comprising orally administering the oral delivery system of any one of embodiments 23 to 41 to said domesticated animal.

43. A method of delivering live mammalian cells to the intestinal tract of an individual comprising orally administering the oral delivery system of any one of embodiments 23 to 39 to the individual.

44. The method of embodiment 43, wherein the individual is a human.

45. The method of embodiment 43, wherein the individual is a domesticated animal.

46. The method of forming a matrix, gel or, excipient to embed mesenchymal stem cells wherein said matrix is comprised of agar or hydrogel.

47. The method of embodiment 46, wherein the hydrogel is comprised of a mixture of alginate and methyl cellulose.

EXAMPLES

The following illustrative examples are representative of embodiments of compositions and methods described herein and are not meant to be limiting in any way.

Example 1—Production of Live Stem Cell Compositions for Oral Delivery

First, the live stem cells were packaged into the formulated monophasic enteric capsule or capsule-in-capsule biphasic vehicle prior to evaluation. Briefly, capsules were prepared as follows: gelatin capsules (size 000 and 00) are filled with 250 mg of crystal violet and a stainless-steel bar (6.3 mm°-12 mm). Loaded capsules were then arranged in a dipping tray and suspended in a pre-prepared EUDRAGIT® L100-55 (e.g., methacrylic acid and ethyl acrylate) mixture (EUDRAGIT® L100-55, 9.0 g; polyethylene glycol 400, 1.4 g; Tween 80, 0.1 g; acetone, 38 ml; isopropyl alcohol, 57 ml; and water, 5 ml) for 15 s, permitting ⅔ of the capsules' surface to be coated and then allowed to dry for 30 min. Capsules were then inverted and re-inserted into the dipping tray and the remaining ⅓ of the capsules' surface was coated. Capsules were subsequently placed on the laboratory bench at ambient temperature and allowed to completely dry for 72 h. Specific residual solvent analysis was not performed; however, all coated capsules were free of acetone odor after 72 h of drying. For monophasic capsules the 000 were layered with live cells [5 million total live cells] whereas for the capsule-in-capsule the coated 00 capsules were layered with cells [2.5 million] prior to placing within the cell layered 000 capsules [2.5 million]. In a series of experiments, we then tested the in vitro enteric protective ability of both the DRcaps® (e.g., hydroxypropyl methylcellulose (HPMC) and gelatin capsules coated with EUDRAGIT® L100-55 either once, twice, thrice, or four times. Uncoated gelatin capsules or commercially available DRcaps® capsules used for controls were loaded with crystal violet and the stainless-steel bar but were not EUDRAGIT® L100-55 coated. Finally, capsules were also loaded with 5 million human MSC aggregates. Subsequently, a paddle system dissolution apparatus was used in accordance with pharmacopoeia standards. In these experiments, a dissolution bath (USP 23 type II Apparatus Vankel VK6010, Varian Inc., Palo Alto, Calif., USA) was assembled and pre-warmed to 37° C. A volume of 400 ml of 0.1 mol/L HCl (pH 1.0) was placed into 3° C.—dissolution cups and rotation is set at 100 r/min. Enteric protection/capsule integrity, as measured by visual detection after release of crystal blue dye and in parallel unstained cells, was assessed at 60, 90, and 120 min. At the 120-min mark, 200 ml of serum-free MSC growth medium pH 7.5 was added to the cups, effectively adjusting the pH to 7.0, representative of human intestinal and cell growth conditions and also in accordance with the pH range (6.8-8.0) as accepted by the U.S. Food and Drug Administration Guidance for Industry (www.fda.gov/downloads/drugs/guidancecomplianceregulatoryinformation/guidances/ucm070237.pdf). Integrity was again monitored until the capsule had disintegrated (n>3 for each different capsule coating types)>4 hrs.

Example 2—Viability of Stem Cells in Matrix

Figure 4:
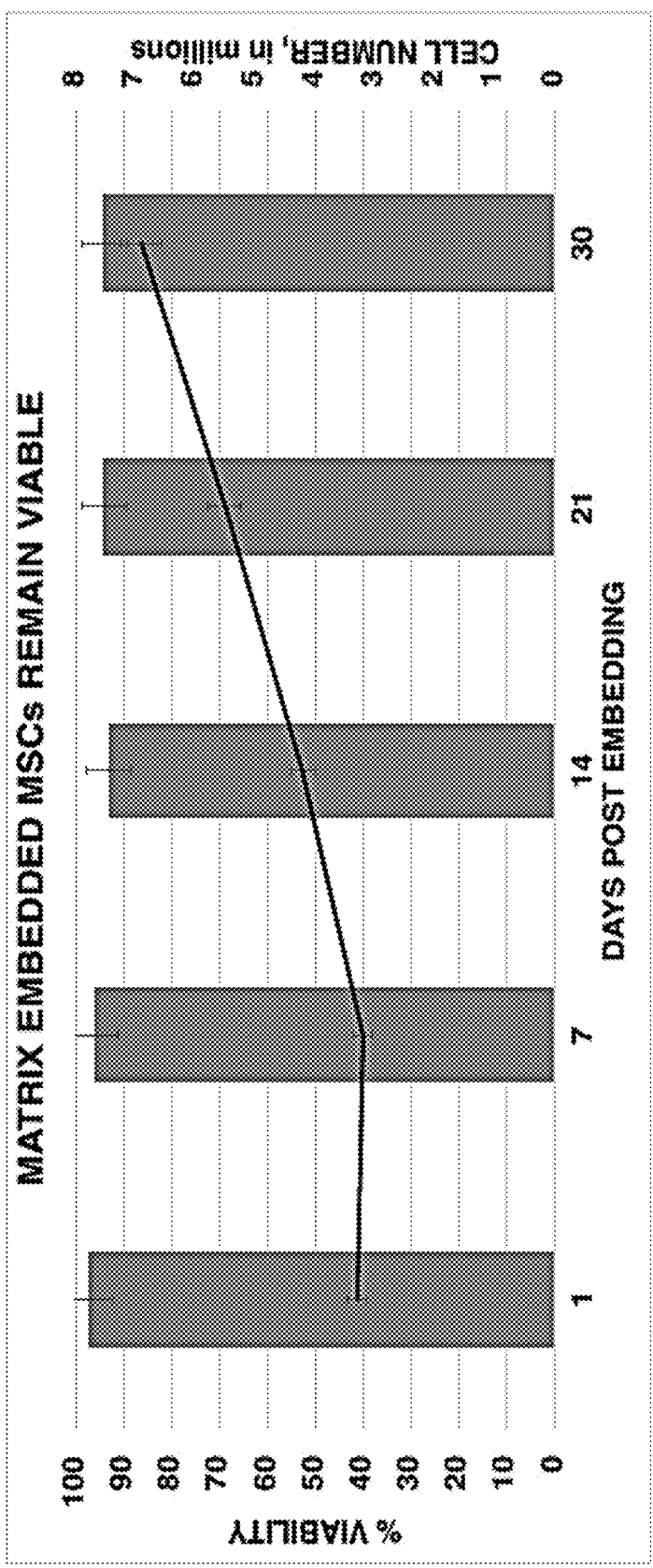
FIG. 4 illustrates that mesenchymal stem cell aggregates remain viable in matrix. As indicated, matrix embedded MSCs remained at around 95% viability throughout the experiment (bars). Cell density approximately doubled under these conditions throughout the culture period (line).

FIG. 4 illustrates that mesenchymal stem cell aggregates remain viable in matrix. Under an embedding condition of about $5\times10^6$ aggregated cells suspended in 0.4% w/v agar-agar per well of a round bottom 96-well plate, experiments were designed to assess cell viability during a 30-day incubation period. Matrix embedded cells were cultured as indicated for 1, 7, 14, 21, and 30 days. Cell number (line) and viability (bars) were determined by trypan blue exclusion assay after dissociation of cells and counting on a hemocytometer. As indicated, matrix embedded MSCs remained at around 95% viability throughout the experiment (bars). Cell density approximately doubled under these conditions throughout the culture period (line).

FIGS. 5 to 8, show data from experiments to evaluate characteristics of live cell containing capsules. Because live cells are only released from capsules after pH-regulated cell release, these experiments simulate the pH changes to which capsules are exposed as they travel down the oral cavity into the ileum and colon. In these experiments, live cell [$5\times10^6$ cells/ea] loaded enteric capsules as indicated were treated similarly to expected pH changes of the capsules traveling down the oral cavity and into the ileum and colon. Thus, a 2 hr pH=1 incubation was followed by a >2 hr pH=7.5 neutralization wherein the cells were recovered and assayed for the functional marker cxcl9 as previously described. See Waterman R. S. et al. "New mesenchymal stem cell (MSC) paradigm: polarization into a pro-inflammatory MSC1 or an immunosuppressive MSC2 phenotype." *PLoS One*. 010 April 26; 5(4). The enteric capsules did not release their payloads until after reaching the neutralized pH. The figure shows cell numbers by trypan blue assay for the recovered cells from each sample. Uncoated capsules released cell contents after low pH dissolution whereas enteric coated capsules retained cells until neutral pH.

Figure 5:
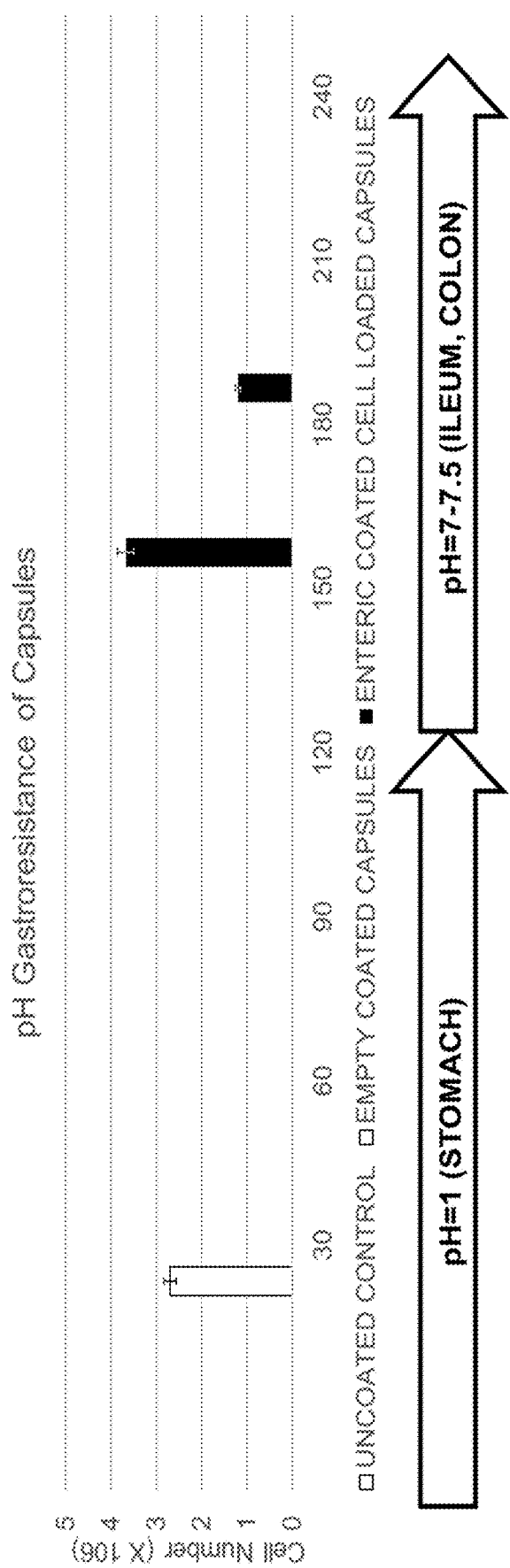
FIG. 5 shows that live cells are only released from capsules after exposure to the pH of the small intestines.
Figure 6:
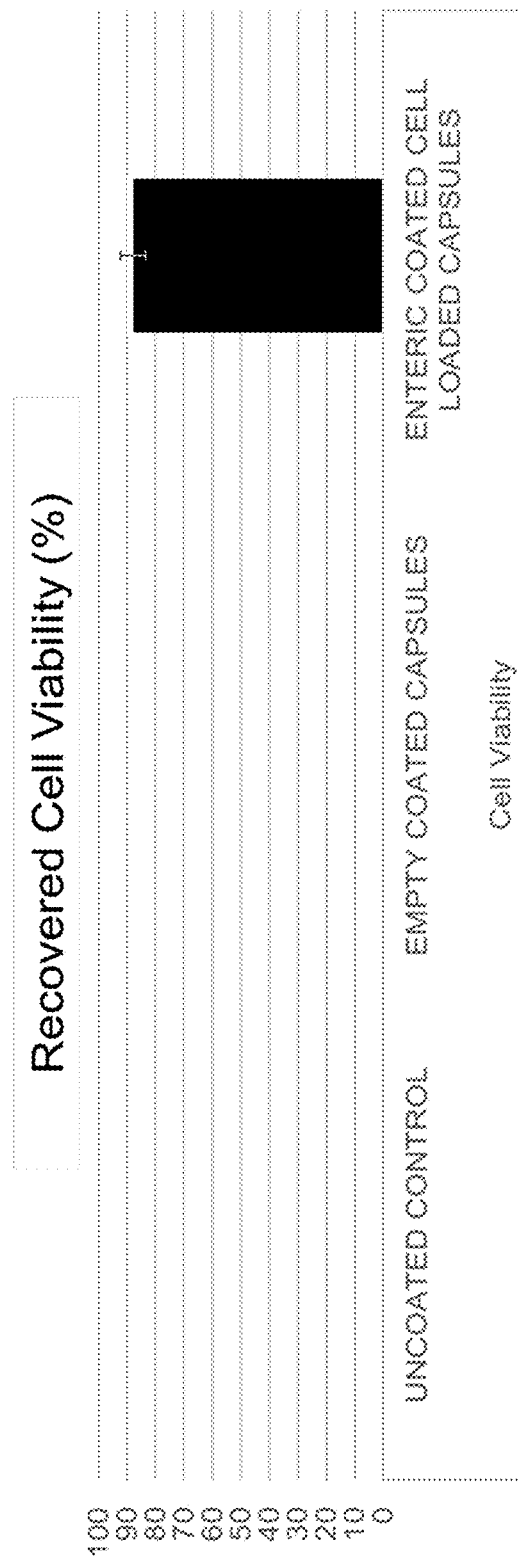
FIG. 6 shows that mesenchymal stem cells as released in FIG. 5 remain viable post pH-regulated release.

Along with cell release and viability, the cell immune regulatory capabilities were monitored. Cell count was measured by trypan blue exclusion assay and immune modulation by cxcl9 gene expression qPCR assay as described previously (Waterman et. al 2010). FIG. 5 shows cell numbers by trypan blue assay for the recovered cells from each sample. The enteric capsules did not release their payloads until after reaching the neutralized pH. By contrast, uncoated capsules released their cell contents after low pH dissolution. FIG. 6 illustrates the results when cell count and viability was measured by trypan blue exclusion assay. Samples were treated in Trypan Blue dye of an acid azo exclusion medium by preparing a 1:1 dilution of the cell suspension using a 0.4% Trypan Blue solution. Blue cells are scored as non-viable cells and unstained ones are scored as viable.

Figure 7:
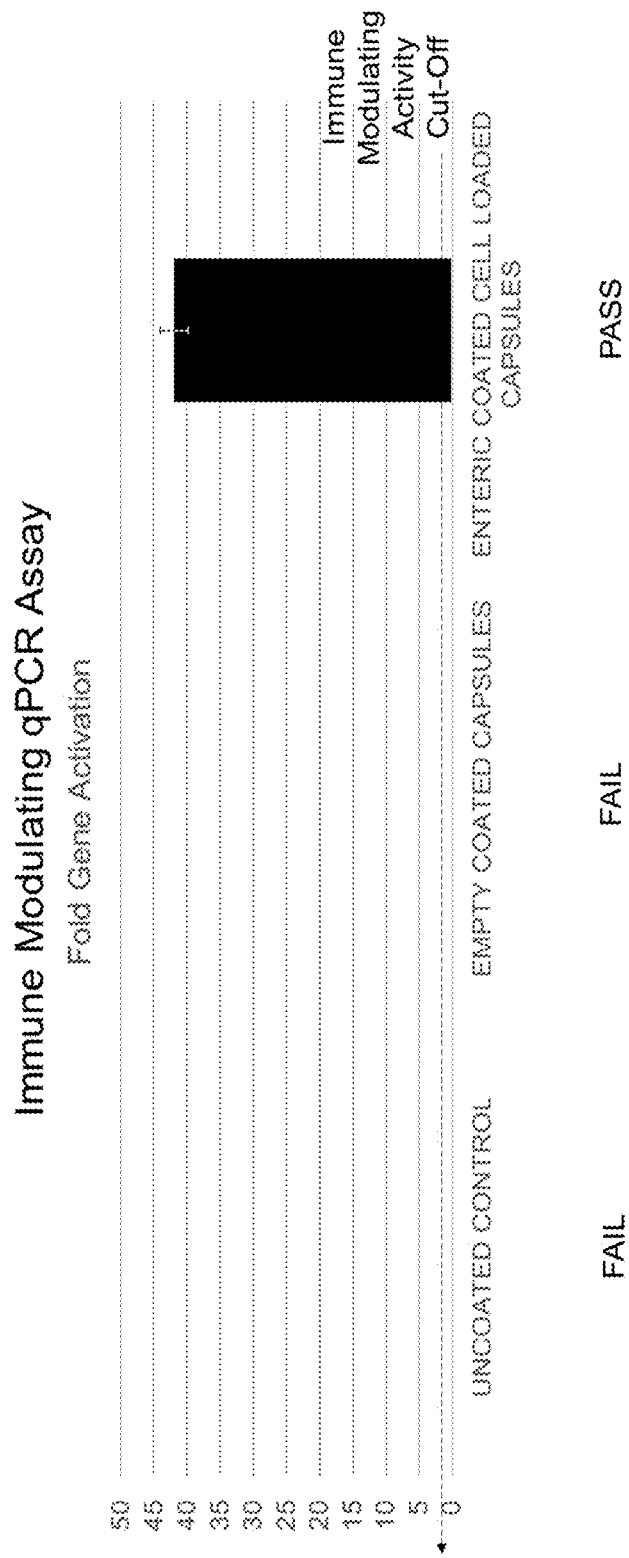
FIG. 7 shows that mesenchymal stem cells retain immune modulating activity post pH-regulated release. Based on previous work, gene activation greater than 2-fold represents a PASS whereas below 2 is a FAIL in immune modulating activity.

Furthermore, FIG. 7 displays immune modulation as assessed by cxcl9 gene expression qPCR assay as described previously. Both cell viability and immune modulating activity were retained to 89% and 85% capsule-in-capsule levels, respectively. Thus, mesenchymal stem cells remain viable and retain immune modulating activity post pH-regulated release.

Example 3—Oral Delivery of Live Mammalian Cells Improves Symptoms in a Mouse Model of Crohn's Like Disease Pre-clinical research studies were conducted to test live cell oral capsule dosage and dosing regimens. A mouse model that develops Crohn's like disease was used. See Pizzaro et al. "Mouse models for the study of Crohn's disease" Trends Mol Med. 2003 May; 9(5):218-22. This is an accepted mouse model that develops Crohn's like disease similar to humans.

Figure 8:
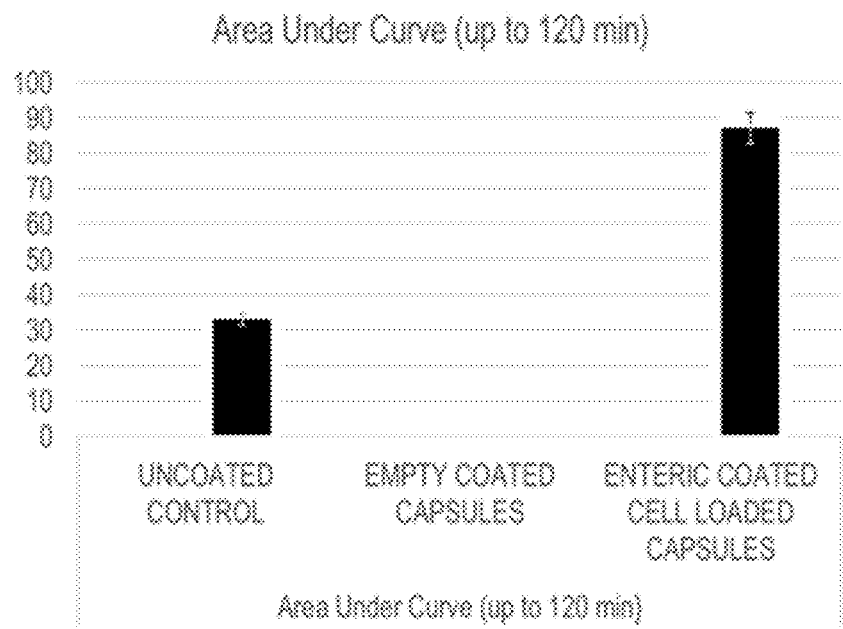
FIG. 8 shows that biodistribution of orally delivered human mesenchymal stem cells in enteric coated capsules can be used to assess cell release from enteric coated capsules. The left bar graph depicts representative cell numbers ($\times 10^3$). The right bar graph depicts the representative area under the curves (AUC) up to 2 hrs.
Figure 8:
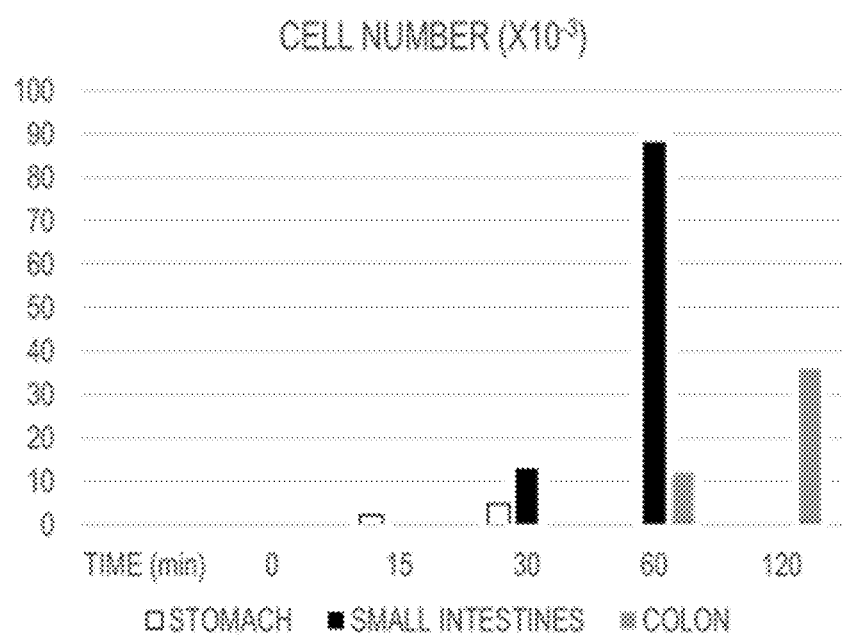

The biodistribution of orally delivered human mesenchymal stem cells in enteric capsules was quantified. BALB/c mice were administered with MSC-loaded enteric capsules per os. The alimentary canal was subsequently harvested after 15 minutes, 30 minutes, 1 hour, and 2 hours. RNA was extracted from the tissue and RT-qPCR analyses of human genomic GADPH over the murine GAPDH as previously described (Bartosh et al., 2010). FIG. 8 (bottom) depicts representative cell numbers. FIG. 8 (top) depicts the area under the curve (AUC) for up to 2 hours.

Histologic evaluation was also performed on H&E-stained sections fixed in 10% formalin by pathologists at the University of California, San Diego (UCSD). Quantification of intestinal lesions was performed in a blinded study using a validated score system: 0 denoted normal histology while 3 denoted maximum severity of histologic changes. The study also took into account three different components of these tissues: active (which harbor neutrophil infiltrates), chronic (which harbor monocyte, B- and T-cell counts), and villus distortion (which exhibit a villus architecture.) The sum of all 3 individual components was expressed as the total score. In sum, the histologic scores showed that MSC therapy alleviated disease in a Crohn's-like ileitis mouse model.

Figure 9:
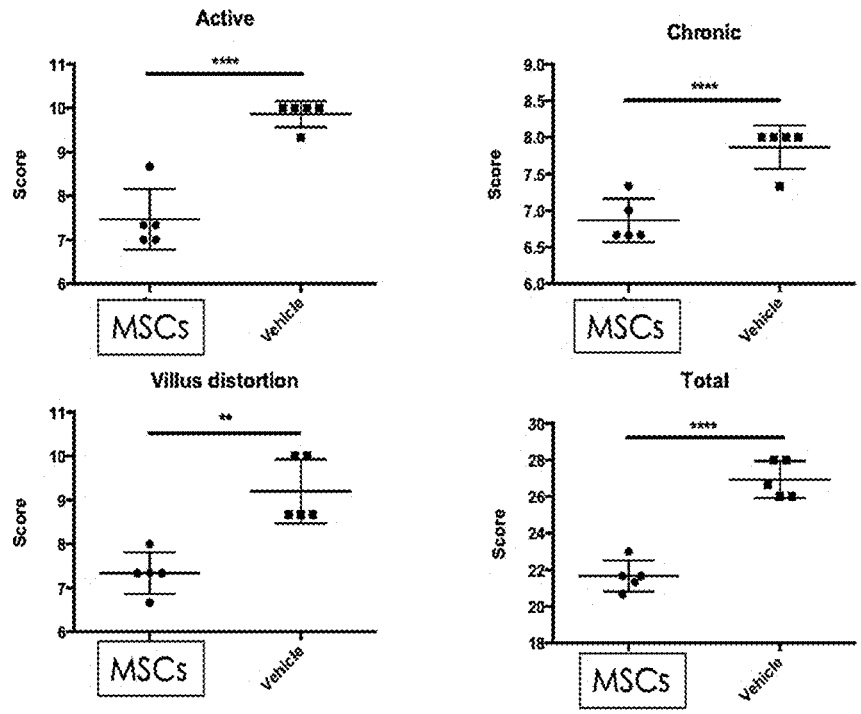
FIG. 9 illustrates histologic scoring of mice treated with oral MSC therapy in a Crohn's-like ileitis mouse model.
Figure 9:
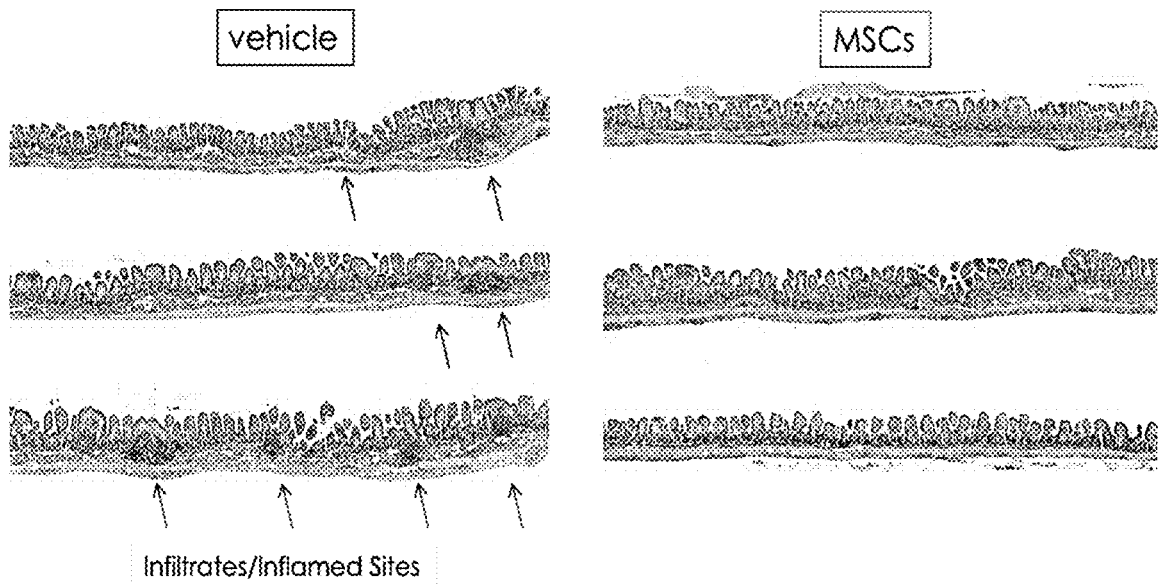

FIG. 9 (top) depicts quantitative histological scoring of treated vs vehicle treated mice. FIG. 9 (bottom) depicts exemplary micrographs of intestinal section quantified above.

Following oral administration of uncoated and coated capsules in mice, the pharmokinetic parameters for live cells was measured. The maximum release profile of cells was expressed as hours elapsed for maximum recovery of cells, and cell viability was assessed by trypan blue excursion assay. Finally, cell potency was assessed by cDNA expression in recovered cells of the anti-inflammatory marker cxcl9. The summary of these results is depicted in FIG. 10

The live cells cross the intestinal barrier in a manner similar to their crossing of an analogous mucosal layer in intranasal delivery of cells. MSCs use a mechanism described as angiopellosis to gain access into the circulation. Subsequently the live cells track to the targeted sites whereby both by cell-cell interactions and by bioactive factor secretion they deliver their therapeutic benefit. These include attenuation of inflammation (immune modulation-recruitment of homeostatic immune cells, decreased pro-inflammatory factors and increased anti-inflammatory ones), provision of anti-oxidants (increased GSH, decreased transferrin, lipid peroxidation), and restoration of aging tissues (recruitment of additional stem and tissue healing cells).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A composition of live mammalian cells formulated for oral delivery to an individual, the composition comprising (a) an enteric coating, (b) a matrix comprising about 1.0% to about 2.0% methyl cellulose and about 1.0% to about 2.0% alginate gel, and (c) a plurality of live mammalian cells, wherein the plurality of live mammalian cells is suspended in the matrix, and wherein the enteric coating surrounds the live mammalian cells suspended in the matrix, wherein the live mammalian cells maintain viability in the intestine of the individual.

2. The composition of claim 1, wherein the matrix comprises about 1.3% to about 1.8% methylcellulose and about 1.3% to about 1.8% alginate gel.

3. The composition of claim 2, wherein the matrix comprises about 1.5% methylcellulose and about 1.5% alginate gel.

4. The composition of claim 1, wherein the methyl cellulose and alginate gel are present at a ratio of about 1:1.

5. The composition of claim 1, wherein the enteric coating comprises methyl methacrylate-methacrylic acid copolymer (1:1).

6. The composition of claim 1, wherein the enteric coating consists essentially of methyl methacrylate-methacrylic acid copolymer (1:1).

7. The composition of claim 1, wherein the plurality of live mammalian cells comprises at least 10,000 live cells.

8. The composition of claim 1, wherein the plurality of live mammalian cells comprises human cells, canine cells, bovine cells, feline ells, porcine cells, equine cells, or ovine cells.

9. The composition of claim 1, wherein the plurality of live mammalian cells comprises at least two types of cells.

10. The composition of claim 1, wherein the plurality of live mammalian cells comprises multipotent cells.

11. The composition of claim 10, wherein the multipotent cells comprise mesenchymal stem cells.

12. The composition of claim 11, wherein the mesenchymal stem cells are Type 2 mesenchymal stem cells.

13. The composition of claim 1, wherein the plurality of live mammalian cells comprise immune cells.

14. The composition of claim 1, wherein the composition preserves the viability of the plurality of live mammalian cells above about 80% viability for at least 14 days at 24° C.

15. The composition of claim 1, wherein the matrix further comprises an extracellular matrix protein.

16. A method of treating a gastrointestinal inflammatory or autoimmune disorder in an individual comprising administering a dose of the composition of claim 1 to the alimentary canal of an individual, thereby treating the gastrointestinal inflammatory or autoimmune disorder in the individual.

17. The method of claim 16, wherein the individual is a human, a dog, a cat, a pig, a horse, a cow, or a sheep.

18. The method of claim 16, wherein the inflammatory or autoimmune disorder comprises inflammatory bowel disease or Crohn's disease.

19. A method of making a composition of live mammalian cells formulated for oral delivery comprising admixing a plurality of live mammalian cells with a matrix comprising about 1.0% to about 2.0% methyl cellulose and about 1.0% to about 2.0% alginate gel to provide a cell-matrix, and applying an enteric coating to the cell-matrix.

* * * * *